(12) United States Patent
Gasper et al.

(10) Patent No.: US 7,781,187 B2
(45) Date of Patent: Aug. 24, 2010

(54) FLUORESCENT DYES

(75) Inventors: Susan Marie Gasper, Corning, NY (US); Mingqian He, Painted Post, NY (US); Fang Lai, Painted Post, NY (US); Thomas Mark Leslie, Horseheads, NY (US); Helen Samson, Granby, CT (US)

(73) Assignee: Corning Incorporated, Corning, NY (US)

( * ) Notice: Subject to any disclaimer, the term of this patent is extended or adjusted under 35 U.S.C. 154(b) by 1209 days.

(21) Appl. No.: 11/324,394

(22) Filed: Dec. 30, 2005

(65) Prior Publication Data
US 2007/0154980 A1 Jul. 5, 2007

(51) Int. Cl.
G01N 33/52 (2006.01)
C07D 277/08 (2006.01)
(52) U.S. Cl. ..................... 435/40.5; 548/146
(58) Field of Classification Search ............... 435/40.5; 548/146
See application file for complete search history.

(56) References Cited

U.S. PATENT DOCUMENTS

| | | | |
|---|---|---|---|
| 4,925,770 A * | 5/1990 | Ichimura et al. ......... 430/273.1 |
| 4,981,977 A | 1/1991 | Southwick et al. ......... 548/455 |
| 5,191,073 A | 3/1993 | Corey et al. ..................... 17/4 |
| 5,436,134 A | 7/1995 | Haugland et al. ............. 435/34 |
| 5,527,688 A | 6/1996 | Mallia ......................... 435/15 |
| 5,569,766 A | 10/1996 | Waggoner et al. ............. 417/6 |
| 5,658,751 A | 8/1997 | Yue et al. ...................... 435/34 |
| 5,986,086 A | 11/1999 | Brush et al. ............. 536/26.26 |
| 5,994,143 A | 11/1999 | Bieniarz et al. ............... 436/91 |
| 6,054,272 A | 4/2000 | Glazer et al. ................... 435/6 |
| 6,067,186 A | 5/2000 | Dalton et al. ................ 359/321 |
| 6,348,599 B1 | 2/2002 | Cummins et al. ............ 548/455 |
| 6,403,807 B1 | 6/2002 | Singh et al. .................. 548/455 |
| 6,458,966 B1 | 10/2002 | Griffiths et al. ............. 548/511 |
| 6,528,319 B1 | 3/2003 | Zhao ............................ 436/94 |
| 6,638,728 B1 | 10/2003 | Desai et al. .................. 435/7.5 |
| 6,664,047 B1 | 12/2003 | Haugland et al. .............. 435/6 |
| 6,750,603 B2 | 6/2004 | Huang et al. ................ 313/483 |
| 2002/0133019 A1 | 9/2002 | Klunk et al. ................ 548/156 |
| 2003/0113765 A1 | 6/2003 | Dempcy et al. ................ 435/6 |
| 2004/0043508 A1 | 3/2004 | Frutos et al. ................ 436/518 |
| 2004/0044219 A1 | 3/2004 | Sandstrom et al. ........ 546/268.4 |
| 2004/0203038 A1 | 10/2004 | Stavrianopoulos et al. ...... 435/6 |
| 2005/0181380 A1 | 8/2005 | Isobe ............................ 435/6 |

FOREIGN PATENT DOCUMENTS

| | | | |
|---|---|---|---|
| BE | 669 934 | 1/1966 | |
| EP | 0246885 A2 | 5/1987 | |
| EP | 0747700 B1 | 12/2001 | |
| EP | 1 547 996 | 6/2005 | .................. 211/48 |
| FR | 2780943 | 4/1981 | |
| WO | WO99/05221 | 2/1999 | |

OTHER PUBLICATIONS

Zeena, S. Conformational Switching and Exciton Interactions in Hemicyanine-Based Bichromophores. J. Am. Chem. Soc. 123 (2001) 7859-7865.*
Tecan Application Note, "Comparison of two different detection techniques for DNA quantification: Absorbance vs. Fluorescence", Doc. No. 391 783, Jul. 2000.
Cosa, G.; Foscaneau, K.-S.; McLean, J.R.N.; McNamee, J.P.; Scaiano, J.C. "Photophysical Properties of Fluorescent DNA-dyes Bound to Single-and Double-stranded DNA in Aqueous Buffered Solution", Photochem. Photobiol. 2001, 73, 585-599.
D.L. Garmaise; G.Y. Paris; J. Komlossy; C.H. Chambers; R.C. McCrae, "Anthelmintic quaternary salts. III. Benzothiazolium Salts", J. Med. Chem. 1969, 12, 30-36.
Q. Fang et al., "Trivalent Boron as an Acceptor in Donor-π-Acceptor-Type Compounds for Single-and Two-Photon Excited Fluorescence", Chem. Eur. J. 2003, 9, 5074-5084.
Perihan Nalbant, Louis Hodgson, Vadim Kraynov, Alexei Toutchkine, Klaus M. Hahn, "Activation of Endogenous Cdc42 Visualized in Living Cells", Science vol. 305 Sep. 10, 2004, 1615-1619.
Alexei Toutchkine, Badim Kraynov, and Klaus Hahn, "Solvent-Sensitive Dyes to Report Protein Conformational Changes in Living Cells", J. Am. Chem. Soc. 2003, 125, 4132-4145.
Lainne Elizabeth Gundy, "Synthesis and Characterization of Substituted Stilbene and Stilbene-Like Compounds", A Thesis 1997 i-xiii, 1-91.

* cited by examiner

Primary Examiner—Kamal A Saeed
Assistant Examiner—Samantha L Shterengarts
(74) Attorney, Agent, or Firm—Tina N. Thompson

(57) ABSTRACT

Fluorescent dyes useful for detecting a target material in biological assays an electron donating moiety which is linked by a conjugated π-electron bridge to an electron accepting moiety. The π-electron bridge includes at least one carbocyclic ring structure or heterocyclic ring structure. The electron accepting moiety is a carboxylic acid, a salt of a carboxylic acid, or has the formula:

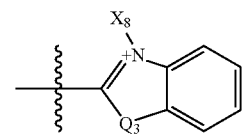

wherein:

$X_8$ is selected from the group consisting of H, $CH_3$, and $(CH_2)_{n_6}\text{-}Z_2^-$, where $Z_2^-$ is a monovalent anion; and $n_6$ is an integer from 1 through 10; and $Q_3$ is O or S.

14 Claims, 3 Drawing Sheets

FLUORESCENT DYES

BACKGROUND

1. Field of the Invention

The present invention relates generally to fluorescent dyes and more particularly to fluorescent dyes useful for the detection and quantitation of a target material in biological assays.

2. Technical Background

Fluorescence labeling is an important technology for detecting biological molecules; for example, antibodies can be labeled with fluorescent dyes. After labeling, the binding of antibodies to their specific target molecules can then be monitored on the basis of a change in fluorescence signal, whether it be an increase or a decrease in fluorescence signal. This change in fluorescence may be detected with a spectrometer, immunofluorescence instrument, flow cytometer, fluorescence microscope, or other detection instrument. In a similar way, DNA sequences can be detected with fluorescence detection instruments after the DNA has been hybridized with a complementary DNA sequence that has been labeled with a fluorescent dye.

Fluorescent dyes offer the opportunity to use color and light to detect and quantify a target material, investigate reactions, and perform assays. Generally, fluorescent dyes with a large Stokes shift (i.e., the difference between fluorescence excitation and emission wavelengths), a low molecular weight and greater stability may permit faster, more sensitive and more selective methods to be utilized.

Commercially available fluorescent dyes have a number of disadvantages. For example, some fluorescent dyes have a quantum yield that is too low and hence lack the sensitivity needed to detect small changes in emission light associated with small amounts of the target material. Other fluorescent dyes have a Stokes shift that is too small to permit detection of emission light without significant detection of excitation light. If the excitation or emission spectrum of the fluorescent dye overlaps with the auto fluorescence of the target material causing a low signal-to-noise ratio, the target material is undetectable. Further, some fluorescent dyes are not stable, having a short shelf-life, so that they are readily bleached and rendered nonfluorescent. Still other fluorescent dyes have an excitation spectrum that does not permit them to be excited by wavelength-limited light sources, such as common lasers and arc lamps. In addition to the above disadvantages, many commercially available fluorescent dyes have the further disadvantage in that they are insoluble in aqueous media. Consequently, they must be dissolved in organic solvents, for example, N,N-Dimethylformamide (DMF) prior to substrate labeling in aqueous media, and these organic solvents can have a deleterious effect upon sensitive substrates. The solubility of the fluorescent dye affects the degree to which they interact with themselves in solution and, when conjugated to substrates, directly influences their light absorption and emission properties. The degree of non-specific staining of cellular matter by a fluorescent dye, which increases noise in the signal-to-noise ratio during fluorescent measurement, is also a function of the dye's hydrophobicity and of the polarity of the fluorescent dye's appended functional groups. Lastly, many fluorescent dyes are difficult to synthesize and expensive to purchase, leading to high-cost detection methods, for example, biological assays for DNA, antigen, monoclonal antibodies, and other assays known in the art.

Although the bases of DNA exhibit an absorbance in the UV spectrum at 260 nm, quantification of DNA by this method requires a large amount of material due to the low sensitivity (high extinction coefficient). It is often quite difficult and costly to obtain sufficient material needed for absorbance detection of DNA alone. As the pharmaceutical and biotech industries continue the trend toward smaller scale and higher throughput assays, more sensitive means of nucleic acid detection and quantitation are required. Assays based on fluorescence are attractive due to their high selectivity and sensitivity, thus allowing for the use of less material.

Cyanine dyes, which exhibit a change in fluorescence intensity upon binding to DNA, are the industry workhorse for biological applications. Cyanine dyes have been developed for nucleic acid detection that are very sensitive over large dynamic ranges. An exemplary cyanine dye is PicoGreen™ (a trademark of Molecular Probes, Inc.) which has a sensitivity for double-stranded DNA (dsDNA) of 250 pg/mL on a microplate reader and a dynamic range ~3 orders of magnitude. PicoGreen™, while not specific for dsDNA over single-stranded DNA (ssDNA), can quantitate dsDNA in the presence of equimolar ssDNA. In addition, it has also been shown that PicoGreen™ can differentiate dsDNA and ssDNA based on its fluorescence lifetime, a sophisticated and cumbersome experiment. Thus, while commercially available cyanine ayes can differentiate between dsDNA and ssDNA, they are not completely satisfactory due to their high cost and small Stokes shifts (typically less than 20 nm). A small Stokes shift causes difficulty in reading the emission signal over the noise in the assay. To compensate for a small Stokes shift, it is necessary to use narrow wavelength laser excitation sources and multiple emission high resolution monochromators, which ultimately results in increased instrument cost.

As a result of the foregoing problems with currently available commercial dyes, fluorescent dyes which can be easily synthesized from relatively inexpensive starting materials, which exhibit a large Stokes shift and which have a low molecular weight are desirable. These properties will permit cleaner detection of the dye emission wavelength over the excitation wavelength, thus eliminating the need for more expensive instrumentation. Fluorescent dyes which have an increased selectivity towards dsDNA over ssDNA, a feature which is important when quantifying dsDNA in a crude reaction mixture (i.e. PCR product mix), are also desirable. Fluorescent dyes which have multiple attachment sites for target material to bind, tethering ability from the multiple attachment sites for attaching the fluorescent dye to a surface, fluorescence in the dry state (requiring no solvent), and a long shelf-life would also be beneficial. Fluorescent dyes soluble in aqueous media which can be manipulated based on the particular application would be especially advantageous.

SUMMARY OF THE INVENTION

One embodiment of the present invention relates to fluorescent dyes having Formula I:

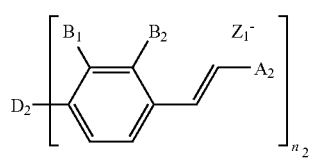

wherein:

$D_2$ is selected from the group consisting of an electron-donating moiety; and $B_1$ and $B_2$ can be the same or can be different and are selected from the group consisting of H, OH, $NH_2$, Cl, and F; and $A_2$ is an electron-accepting moiety having formula:

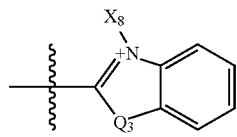

wherein:

$X_8$ is selected from the group consisting of H, $CH_3$, and $(CH_2)_{n6}\text{-}Z_2^-$, where $Z_2^-$ is a monovalent anion, and further provided that when $Z_2^-$ is present, then $Z_1^-$ is absent; and $n_6$ is an integer from 1 through 10; and $Q_3$ is O or S; and $Z_1^-$ is a monovalent anion, and further provided that when $Z_1^-$ is present, then $(CH_2)_{n6}\text{-}Z_2^-$ is absent; and $n_2$ is an integer from 1 through 2.

Another embodiment of the present invention relates to fluorescent dyes having Formula IV:

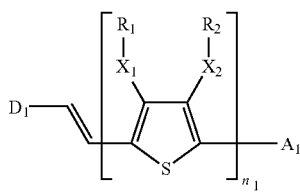

wherein:

$D_1$ is an electron donating moiety; and $X_1$ and $X_2$ can be the same or can be different and are selected from the group consisting of H, $CH_3$, OH, SH, NH, Se, F, Cl, and $CH_2$, provided that $R_1$ and $R_2$ are absent when X is H, F, or Cl; or when X is not F or Cl, then:

$R_1$ and $R_2$ can be the same or can be different and are selected from the group consisting of H, $CH_3$, and $CH_2$-Q, where Q is selected from the group consisting of OH, SH, and NH, or $R_1$ and $R_2$ form a carbocyclic ring structure or a heterocyclic ring structure having at least one ring atom selected from the group consisting of O, N, and S;

$n_1$ is an integer from 1 through 2; and $A_1$ is an electron accepting moiety selected from the group consisting of a carboxylic acid and a salt of the carboxylic acid.

Another embodiment of the present invention relates to an analytical device for detecting a target material in a sample. The analytical device has at least one reaction area which is covalently labeled with a dye that fluoresces when in contact with a specific target material. The reaction area(s) is (are) disposed for contact with a sample. The analytical device has at least one detector in proximity to the reaction area(s) for detecting the presence or absence of fluorescence.

Another embodiment of the present invention relates to a method of synthesizing the fluorescent dye of Formula I:

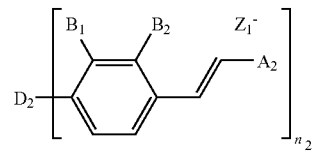

the method comprising:

adding excess iodomethane to methylbenzthiazole;

isolating methylbenzthiazole salt;

dissolving the methylbenzthiazole salt in methanol to form a methylbenzthiazole solution in methanol;

adding a substituted benzaldehyde and piperidine to the methylbenzthiazole solution in methanol; and isolating the reaction product and recrystallizing a solid from the solution;

wherein in Formula I;

$D_2$ is selected from the group consisting of an electron-donating moiety; and $B_1$ and $B_2$ can be the same or can be different and are selected from the group consisting of H, OH, $NH_2$, Cl, and F; and $A_2$ is an electron-accepting moiety having formula:

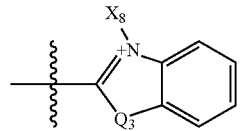

wherein:

$X_8$ is selected from the group consisting of H, $CH_3$, and $(CH_2)_{n6}\text{-}Z_2^-$, where $Z_2^-$ is a monovalent anion, and further provided that when $Z_2^-$ is present, then $Z_1^-$ is absent; and $n_6$ is an integer from 1 through 10; and $Q_3$ is O or S; and $Z_1^-$ is a monovalent anion, and further provided that when $Z_1^-$ is present, then $(CH_2)_{n6}\text{-}Z_2^-$ is absent; and $n_2$ is an integer from 1 through 2.

It will be noted that the commonality of the fluorescent dyes of the present invention is an electron-donating moiety which is linked by a conjugated π-electron bridge to an electron-accepting moiety. The π-electron bridge includes at least one carbocyclic ring structure or heterocyclic ring structure. The electron-accepting moiety is a carboxylic acid, a salt of a carboxylic acid, or has the formula:

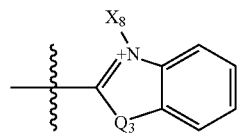

wherein:

$X_8$ is selected from the group consisting of H, $CH_3$, and $(CH_2)_{n6}\text{-}Z_2^-$, where $Z_2^-$ is a monovalent anion, and further provided that when $Z_2^-$ is present, then $Z_1^-$ is absent; and $n_6$ is an integer from 1 through 10; and $Q_3$ is O or S.

The fluorescent dyes of the present invention, each of which has this general structure, have been shown to exhibit an increase or decrease in emission intensity upon interaction with DNA depending on the identity of electron-donating and electron-accepting moieties. Although most commercial dyes show a positive response or an increase in emission signal when interacting with DNA, examples of biological assays with a negative response or a decrease in emission signal exist; for example, the IQ® (a trademark of Pierce Biotechnology, Inc.) Kinase Assay Platform. The fluorescent dyes having this general structure have also been shown to exhibit a preference towards dsDNA over ssDNA. The dyes of the present invention possess a larger Stokes shift than most commercial dyes for DNA quantification; a feature which should make them more compatible with less sophisticated, and therefore less expensive, instrumentation without sacrificing sensitivity.

Additional features and advantages of the invention will be set forth in the detailed description which follows, and in part will be readily apparent to those skilled in the art from the description or recognized by practicing the invention as described in the written description and claims hereof, as well as the appended drawings.

It is to be understood that both the foregoing general description and the following detailed description are merely exemplary of the invention, and are intended to provide an overview or framework to understanding the nature and character of the invention as it is claimed.

The accompanying drawings are included to provide a further understanding of the invention, and are incorporated in and constitute a part of this specification. The drawings illustrate one or more embodiment(s) of the invention and together with the description serve to explain the principles and operation of the invention.

BRIEF DESCRIPTION OF THE DRAWINGS

The invention is best understood from the following detailed description when read with the accompanying drawing figures.

DETAILED DESCRIPTION

Figure 1:
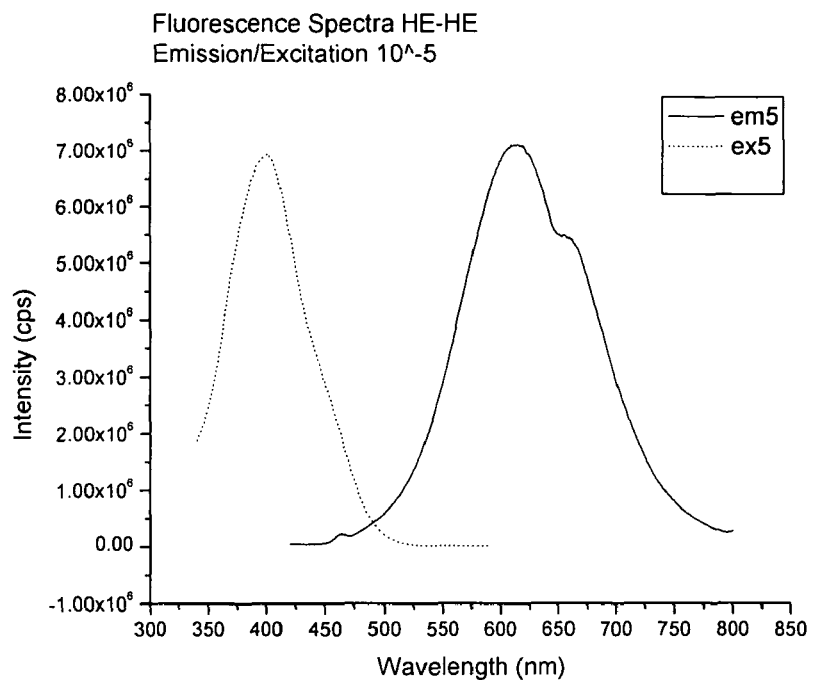
FIG. 1 is a graph showing excitation and emission spectra of a particular dye in buffer.

As used herein:

the phrase "electron-donating moiety" is used synonymously with "electron donator" or "electron donor" and refers to substituents which contribute electron density or may further include H, F, or CL;

the phrase "electron-accepting moiety" is used synonymously with "electron acceptor" or "electron withdrawing" and refers to substituents which attract electron density;

the term "auxochrome" refers to a saturated group with nonbonded electrons which, when attached to a chromophore, alters both the wavelength and intensity of an absorption; and the term "substituent" refers to an atom or group that replaces another atom or group in a molecule.

The invention will be further clarified by the following examples which are intended to be exemplary of the invention.

One embodiment of the present invention relates to fluorescent dyes having Formula I:

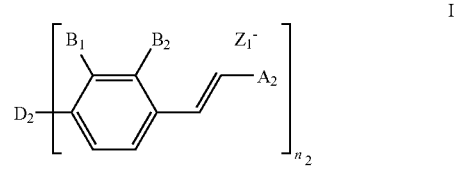

wherein:

$D_2$ is selected from the group consisting of an electron-donating moiety; and $B_1$ and $B_2$ can be the same or can be different and are selected from the group consisting of H, OH, $NH_2$, Cl, and F; and $A_2$ is an electron-accepting moiety having formula:

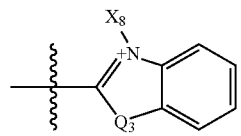

wherein:

$X_8$ is selected from the group consisting of H, $CH_3$, and $(CH_2)_{n6}\text{-}Z_2^-$, where $Z_2^-$ is a monovalent anion, and further provided that when $Z_2^-$ is present, then $Z_1^-$ is absent; and $n_6$ is an integer from 1 through 10; and $Q_3$ is O or S; and $Z_1^-$ is a monovalent anion, and further provided that when $Z_1^-$ is present, then $(CH_2)_{n6}\text{-}Z_2^-$ is absent; and $n_2$ is an integer from 1 through 2.

Another embodiment of the present invention relates to fluorescent dyes having Formula II:

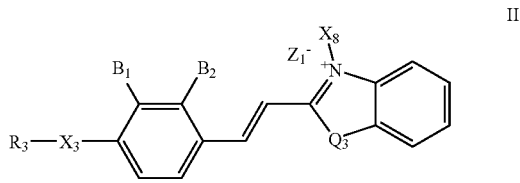

wherein:

$X_3$ is selected from the group consisting of H, $CH_3$, OH, SH, —NH—, —Se—, —O—, —S—, F, Cl, and $CH_2$ provided that $R_3$ is absent when $X_3$ is H, $CH_3$, OH, SH, F or Cl; or when $X_3$ is not H, $CH_3$, OH, SH, F or Cl, then:

$R_3$ is selected from the group consisting of H, $CH_3$, and $(CH_2)_{n4}\text{—}X_6$, where $X_6$ is selected from the group consisting of OH, SH, and $NH_2$, and $n_4$ is an integer from 1 through 10; and $Q_3$ is O or S; and $B_1$ and $B_2$ can be the same or can be different and are selected from the group consisting of H, OH, $NH_2$, Cl, and F; and $X_8$ is selected from the group consisting of H, CH$_3$, and (CH$_2$)$_{n_6}$-Z$_2^-$, where Z$_2^-$ is a monovalent anion, and further provided that when Z$_2^-$ is present, then Z$_1^-$ is absent; and $n_6$ is an integer from 1 through 10; and Q$_3$ is O or S; and Z$_1^-$ is a monovalent anion, and further provided that when Z$_1^-$ is present, then (CH$_2$)$_{n_6}$-Z$_2^-$ is absent.

Exemplary fluorescent dyes having Formula II are as follows, but not limited to:

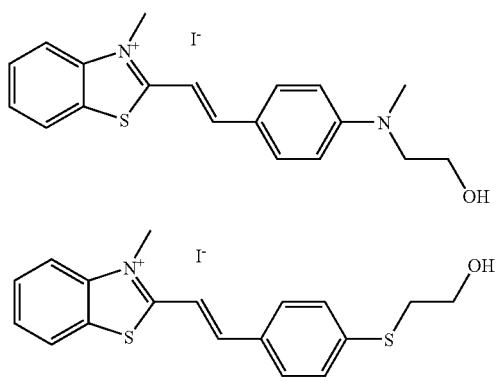

GA

FI

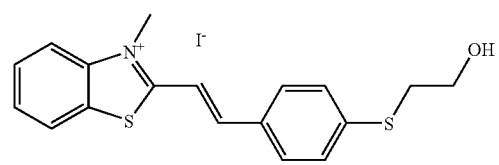

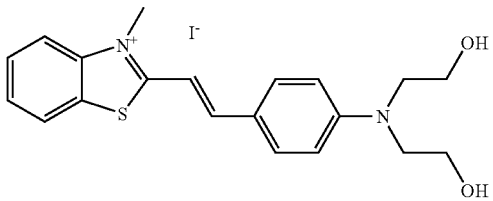

95

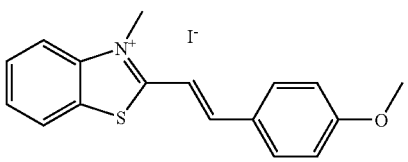

HE

Another embodiment of the present invention relates to fluorescent dyes having Formula III:

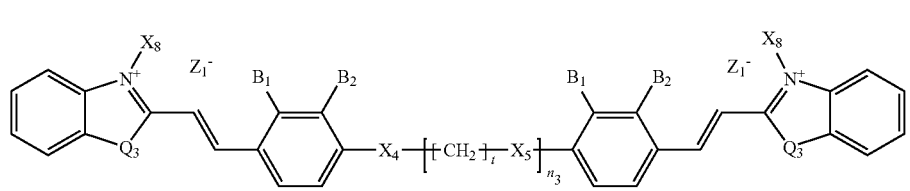

III wherein:

t is an integer from 1 through 8; and

X$_4$ and X$_5$ can be the same or can be different and are selected from the group consisting of O, S, N, NH, NH$_2$ and Se; and $n_3$ is an integer from 1 through 3; and B$_1$ and B$_2$ can be the same or can be different and are selected from the group consisting of H, OH, NH$_2$, Cl, and F; and Q$_3$ is O or S; and Z$_1^-$ is a monovalent anion, and further provided that when Z$_1^-$ is present, then (CH$_2$)$_{n_6}$-Z$_2^-$ is absent; and X$_8$ is selected from the group consisting of H, CH$_3$, and (CH$_2$)$_{n_6}$-Z$_2^-$, where Z$_2^-$ is a monovalent anion, and further provided that when Z$_2^-$ is present, then Z$_1^-$ is absent; and $n_6$ is an integer from 1 through 10.

An exemplary fluorescent dye having Formula III is as follows, but is not limited to:

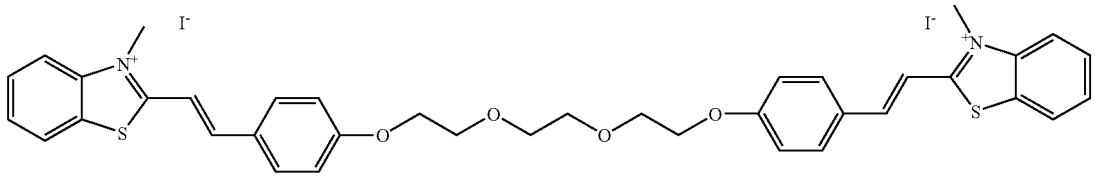

HE—HE

The identity of $Q_3$, in Formula I, Formula II, and Formula III, has been found to influence the fluorescence quantum yield, with the benzthiazole dyes ($Q_3$=S) of the present invention having higher fluorescence. While the exemplary fluorescent dyes shown have $Z_1^-$=I$^-$, any biologically compatible counter ion that is stable and synthetically accessible could be used, for example OH, SH, $HCO_3$, $HSO_3$, $HSO_4$, $H_2PO_4$, $PF_6$, F, CNO, SCN, tetraphenyl borate, $BH_4$, Cl, Br, $BF_4$, 13, $NO_3$, $SO_3$, BrO, $BrO_2$, $BrO_3$, $BrO_4$, IO, $IO_2$, $IO_3$, $IO_4$, ClO, $ClO_2$, $ClO_3$, and $ClO_4$. Preferably $Z_2^-$ is selected from the group consisting of O, S, $CO_2$, $PO_3$, $PF_6$, F, $SO_3$, and $NO_2$.

$B_1$ and $B_2$ in Formula I, Formula II, and Formula III may function as auxochromes, enhancing the fluorescent response of the fluorescent dye by changing the electron density of the fluorescent dye.

The exemplary fluorescent dyes of the present invention, as listed in Table 1 (GA, 95, FI and HE), are synthesized from readily available starting materials. First, excess iodomethane is added to methylbenzthiazole (67 mmol). The reaction mixture is refluxed for 24 hours, after which a methylbenzothiazolium salt is isolated as a pale cream powder by evaporation of the excess iodomethane. The unpurified salt is then dissolved in methanol (10 mL) to which 3.4 mmol of an appropriate auxochrome substituted benzaldehyde and one drop of piperidine is added. The auxochrome substituted benzaldehyde of choice will determine the final properties of the fluorescent dye, particularly the auxochrome chosen will determine the color and solubility of the dye. The resulting mixture is then refluxed for 24 hours. The solid that forms upon cooling is isolated and recrystallized from methanol/water to yield the desired product. The variations on monomeric dye synthesis and exemplary auxochrome substituted benzaldehydes are shown in Table 1.

TABLE 1

| Final product | Substituted benzaldehyde | Final product color |
|---|---|---|
| GA | 4-[(2-hydroxyethyl)methylamino]benzaldehyde | Dark blue |
| FI | 4-[(2-hydroxyethyl)thio]benzaldehyde | |
| 95 | 4-[bis(2-hydroxyethyl)amino]benzaldehyde | Dark green |
| HE | 4-methoxybenzaldehyde | Dark green |

The dimeric cyanine dye HE-HE is synthesized as described above using 4,4'-[1,2-ethanediylbis(oxy-2,1-ethaneediyloxy)]bis-benzaldehyde. This aldehyde is not commercially available and is synthesized as follows: 4-hydroxybenzaldehyde (54 mmol) is dissolved in dry acetone (100 mL) and stirred with potassium carbonate (270 mmol) for 1 hour. 1,2-Bis-(2-iodoethoxy)ethane (10 g) is added dropwise to the reaction and the mixture is heated at reflux for 24 hours. The cooled mixture is poured into water and extracted with ethyl acetate. The combined organic layers are dried over anhydrous magnesium sulfate and concentrated to yield viscous, yellow oil. The crude product is purified by column chromatography using hexane/ethyl acetate as the eluent. An aldehyde is obtained as a cream colored solid.

The fluorescence of the exemplary fluorescent dyes in buffer was examined on a Fluorolog®-3 (a trademark of Spex Industries Inc.) spectrometer. Exemplary excitation and emission spectra are shown in FIG. 1. The fluorescent dyes of the present invention have large Stokes shifts; the excitation and emission maxima are close to or greater than 100 nm apart. Peak wavelengths are tabulated in Table 2 along with two commercially available fluorescent dyes, TOTO-1™ and YO-PRO-3™ (trademarks of Molecular Probes, Inc.). The Stokes shifts of TOTO-1™ and YO-PRO-3™ are small in comparison to the dyes of the present invention.

TABLE 2

| Dye | Excitation max. | Emission max. | Stokes shift |
|---|---|---|---|
| GA | 512 | 587 | 75 |
| FI | 382 | 546 | 164 |
| 95 | 500 | 585 | 85 |
| HE | 385 | 500 | 115 |
| HE—HE | 400 | 616 | 216 |
| TOTO-1 ™* | 514 | 533 | 19 |
| YO-PRO-3 ™* | 612 | 631 | 19 |

*Commercial Dye data from Molecular Probes catalog

Figure 2:
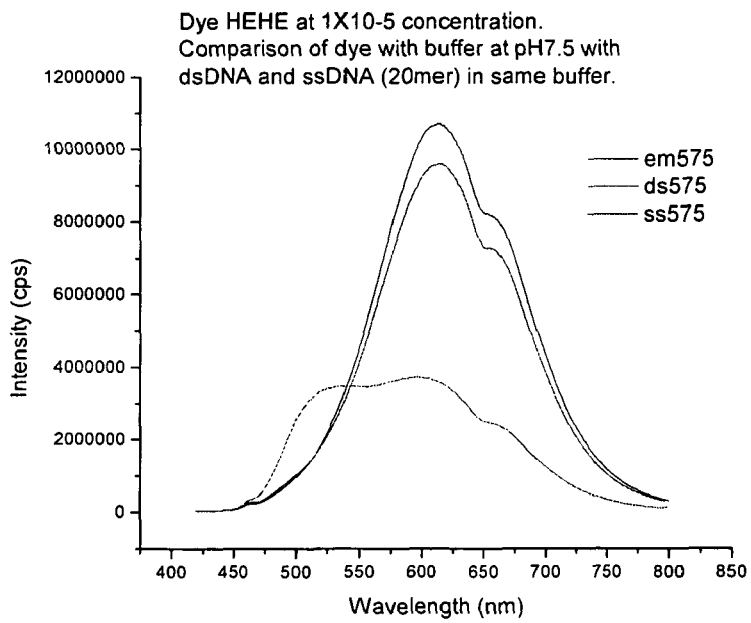
FIG. 2 is a graph showing the effect of ssDNA and dsDNA on HE-HE emission.

FIG. 2 illustrates the effect of ssDNA and dsDNA on dye emission. This effect is most pronounced for the dyes FI and HE-HE. All the dyes reported here show a larger change in emission intensity upon the addition of dsDNA than they do upon the addition of ssDNA; in some cases (GA, 95) this change is positive, in others it is negative (HE, HE-HE, FI).

Emission intensities of the fluorescent dyes of the present invention and TOTO-1™ at $1 \times 10^{-5}$ M in 1×PCR buffer were compared in the absence of DNA (free dye emission) and in the presence of equimolar dsDNA or ssDNA (20 mer) on the fluorescence spectrometer. The emission intensity with dsDNA or ssDNA relative to the free dye emission is tabulated in Table 3.

TABLE 3

| Dye | Free dye rel. to dsDNA | Free dye rel. to ssDNA |
|---|---|---|
| HE—HE | 13.5 | 1.19 |
| FI | 28.7 | 0.98 |
| TOTO-1 ™* | 0.003 | 0.95 |

*Commercially available dye

In this example, the dye FI shows very little change of the emission intensity in the presence of ssDNA but a 28.7 times change in the presence of dsDNA. HE-HE shows a 13.5 times change with dsDNA. The commercially available fluorescent dye, TOTO-1™, shows a much larger change (~3 orders of magnitude) upon interaction with dsDNA (the ratio is smaller because TOTO-1™ emission increases with binding to DNA) and very little change with ssDNA. Although TOTO-1™, shows a high sensitivity to dsDNA, it has a small Stokes shift, which necessitates sophisticated equipment for detection of the emission intensity. It is important to remember that this data is from a research-grade spectrometer; data from a less sophisticated plate reader may be different; in that, the benefit of the dsDNA sensitivity of TOTO-1™ may not be realized over the signal-to-noise in a less sophisticated plate reader. The fluorescent dyes of the present invention have a large Stokes shift allowing the use of less sophisticated equipment for the detection of the emission intensity.

For high-throughput screening of nucleic acids, the dyes may be used in a microwell plate assay. Although in principle plate readers measure fluorescent intensity much like the fluorescence spectrometer, there are several features that are unique due to the sample format (well vs. cuvette) and the instrument optics. For these reasons, sensitivity and linear range of detection for the fluorescent dyes of the present invention were determined in a microplate reader. The Coefficients of Variance in microplate readings for buffer plus dye only for fluorescent dyes of the present invention relative to three leading commercially available fluorescent dyes from Molecular Probes, Inc. at optimal excitation and emission wavelengths are shown in Table 4. The background signal was read for buffer plus dye only at two sample volumes. For a 100 μL/well volume, the background of the commercial dyes shows 76-115% variance while these values are significantly lower for HE-HE and 95. The effect is less pronounced at higher sample volumes, although the fluorescent dyes of the present invention are able to maintain low variance over the two sample volumes and more importantly, at the lower sample volume, allowing improved material utilization of the fluorescent dye and sample. The need for a fluorescent dye with an increased Stokes shift is clear in this example. For detection of the target material in a biological assay, the change in fluorescence needs to be distinguishable from the noise in the system, of which buffer plus dye is a contributor to the noise.

TABLE 4

| Dye | Excitation/Emission wavelengths (nm) | Coefficient of Variance 100 μL/well | Coefficient of Variance 200 μL/well |
|---|---|---|---|
| YOYO/YO-PRO1 ™* | 491/509 | 76 | 32 |
| TOTO-1 ™* | 514/533 | 84 | 12 |
| TO-PRO3 ™* | 642/661 | 115 | 19 |
| HE—HE | 400/660 | 24 | 13 |
| 95 | 504/588 | 12 | 13 |

*Commercially available dyes

The fluorescent dyes shown in Table 5 were titrated with dsDNA in order to determine the sensitivity (lowest detection limit) and dynamic range. A 96-well polystyrene Corning Costar® (a trademark of Corning Incorporated) microwell plate was loaded with 100 μL/well of dye mixed with various levels of dsDNA and incubated at room temperature for 2 hours allowing the mixture to equilibrate. The dye fluorescence was then measured on a SpectraMax® (a trademark of Molecular Devices Corp.) Gemini Plate-reader. Relative fluorescence units (RFU) were then plotted against DNA concentration in pg/μL. The experimental parameters and results for each dye are shown in Table 5. The fluorescent dye HE-HE appears to be more sensitive than commercially available dye TOTO-1™ and exhibits a greater dynamic range. The fluorescent dye of the present invention, 95 is comparable to the commercially available TOTO-1™ in terms of sensitivity but has a larger dynamic range.

TABLE 5

| Dye (conc. μM) | Ex/em wavelengths (nm) | Signal change with dsDNA | Lowest detection limit (ng/well) | Dynamic range |
|---|---|---|---|---|
| HE—HE (0.66) | 400/660 | Decrease | 10 | >3 orders |
| GA (1.0) | 500/595 | Increase | 360 | <2 orders |
| 95 (10) | 504/588 | Increase | 40 | <2 orders |
| TOTO-1 ™ (10)* | 514/533 | Increase | 40 | <1 order |
| YOYO-1 ™ (10)* | 491/509 | Increase | 120 | 1 order |
| TO-PRO-3 ™ (10)* | 642/661 | Increase | 40 | 1 order |
| YO-PRO-1 ™ (10)* | 491/509 | Increase | 120 | <1 order |

*Commercially available dyes

Figure 3:
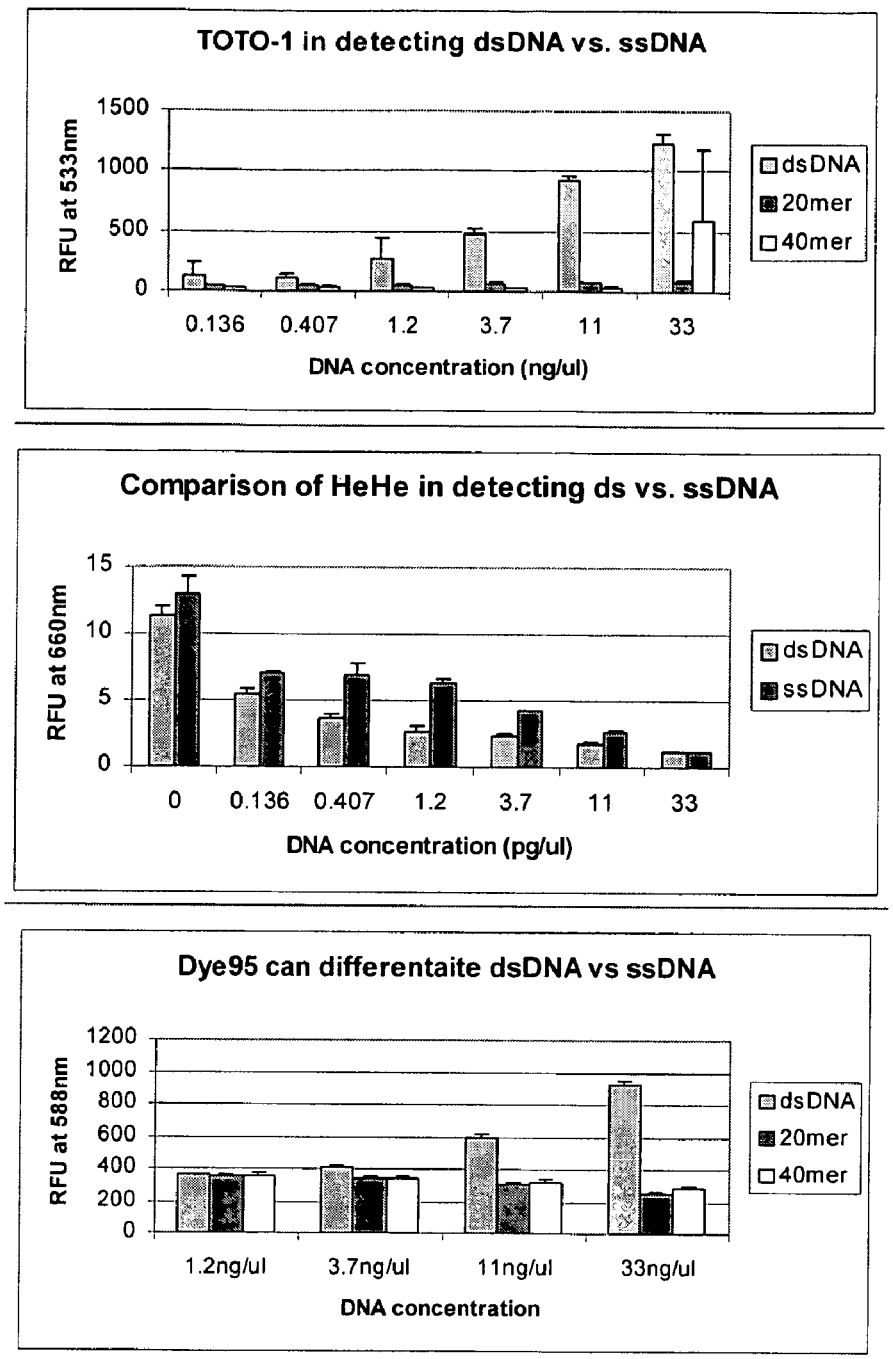
FIG. 3 is three graphs showing dye performance with respect to ss/dsDNA in a plate reader assay.

FIG. 3 illustrates the ssDNA/dsDNA selectivity of the fluorescent dyes of the present invention, HE-HE and 95, versus the commercially available fluorescent dye TOTO-1™ in the plate reader assay. Consistent with the fluorometer data is the superior selectivity of TOTO-1™ towards dsDNA. 95 displays a significant preference for dsDNA, whereas HE-HE is only slightly more sensitive towards dsDNA than ssDNA. By learning more about the binding modes of the disclosed dyes, it should be possible to design and synthesize members of the family optimized for dsDNA detection.

Another embodiment of the present invention relates to fluorescent dyes having Formula IV:

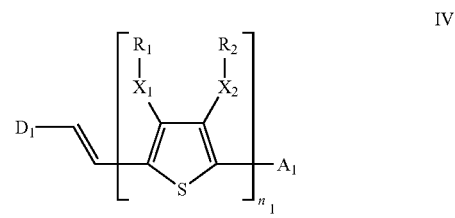

wherein:
$D_1$ is an electron donating moiety; and
$X_1$ and $X_2$ can be the same or can be different and are selected from the group consisting of H, $CH_3$, OH, SH, NH, Se, F, Cl, and $CH_2$, provided that $R_1$ and $R_2$ are absent when X is H, F, or Cl; or
when X is not F or Cl, then:
$R_1$ and $R_2$ can be the same or can be different and are selected from the group consisting of H, $CH_3$, and $CH_2$-Q, where Q is selected from the group consisting of OH, SH, and NH, or
$R_1$ and $R_2$ form a carbocyclic ring structure or a heterocyclic ring structure having at least one ring atom selected from the group consisting of O, N, and S;
$n_1$ is an integer from 1 through 2; and
$A_1$ is an electron accepting moiety selected from the group consisting of a carboxylic acid and a salt of the carboxylic acid.

Preferably, $D_1$ is selected from the group consisting of:

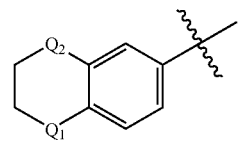

wherein:
$Q_1$ and $Q_2$ can be the same or can be different and are selected from the group consisting of $CH_2$, O, S, and NH;

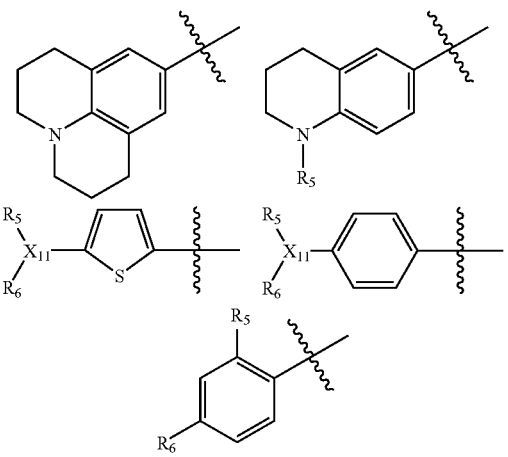

wherein:

$X_{11}$ is selected from the group consisting of O, S, and N; and $R_5$ and $R_6$ can be the same or can be different and are selected from the group consisting of H, $CH_3$, and $(CH_2)_{n5}$—$X_7$, where $X_7$ is selected from the group consisting of OH, SH, and $NH_2$ and $n_5$ is an integer from 1 through 10; and when $X_{11}$ is O or S, then only one of $R_5$ and $R_6$ is present and the other is absent.

Preferably, $A_1$ is selected from the group consisting of:

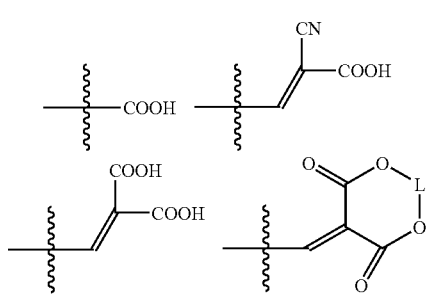

wherein:
M is a monovalent cation;

wherein:
L is a metal.

Fluorescent dyes having Formula IV can be synthesized by the following exemplary schemes:

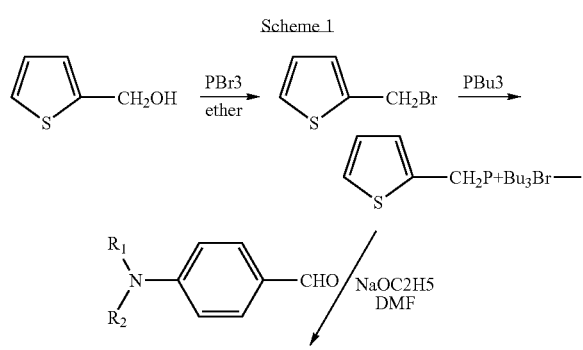

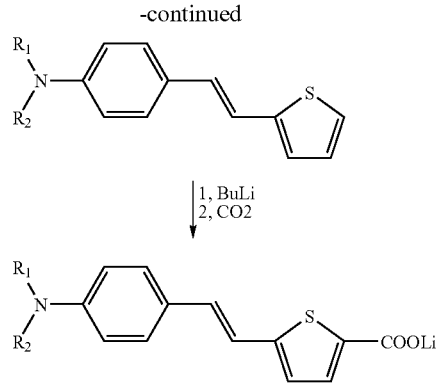

R1 = CH3, CH2CH2OH
R2 = CH3, CH2CH2OH

EXAMPLES

Example 1

General Synthesis for Amination of 2-bromothiophene N,N-dimethylethanolamine

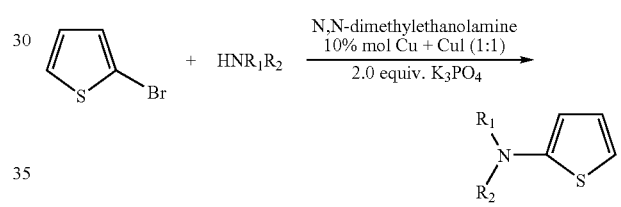

2-Bromothiophene (16.3 g, 0.1 mol), 2-(ethylamino)ethanol (100 ml), Cu metal (0.32 g), CuI (0.85 g), $K_3PO_4$ (42.4 g) were added to a flask fitted with a magnetic stir bar, a condenser and sealed with a septum. The reaction mixture was stirred at 80° C. for 72 hour under nitrogen position pressure. After the reaction cooled to room temperature, 600 ml water was added and mixture was extracted with ethyl ether (3*200 ml). The combined organic layers were then washed with brine and dried over $MgSO_4$. The solvent was removed in vacuo and the residue was purified by flash chromatography on silica gel eluted with hexane/EtoAc (1:1). The product was obtained as a liquid. Examples of Amination of 2-bromothiophene are shown in Table 7.

TABLE 7

| Entry | R1 | R2 | Product | Temperature/Time | Yield(%) |
|---|---|---|---|---|---|
| 1 | —$CH_3$ | —$CH_2CH_2OH$ | | 80/24 | 68.8 |
| 2 | -$CH_2CH_2OH$ | —$CH_2CH_2OH$ | | 80/24 | 51.87 |

Example 2

General Synthesis of 2-bromomethylthiophene

Tribromide phosphorus (PBr$_3$, 54.2 g, 0.2 mol) was added dropwise at 0° C. to 2-hydroxymethylthiophene (50.0 g, 0.44 mol) in ethyl ether (300 mL). This mixture was stirred overnight at room temperature and poured into saturated NaHCO$_3$ solution (400 mL). The organic layer was separated and washed by NaHCO$_3$ solution (2×100 mL) and water (100 mL). The organic was dried over MgSO$_4$. After evaporating the solvent, the target compound was obtained and used immediately without further purification. Yield 72.0 grams, 92.8%.

Example 3

General Synthesis of 2-thienylmethyltributylphosphonium bromide 2-bromomethylthiophene (72 g, 0.41 mol) was dissolved into toluene (400 mL). To this solution, tributylphosphine (82 g, 0.41 mol) was added. This mixture was heated to 90° C. overnight. This mixture was cooled to room temperature and the solid was filtered. The solid was washed by ethyl ether (200 mL) to give 142.3 grams, (92.3% yield).

Example 4

General synthesis of 4-[N,N-dimethylaminophenylethenyl]thiophene 2-thienylmethyltributylphosphonium bromide (20.9 g, 0.055 mol) and 4-N,N-dimethylaminophenylaldehyde (7.5 g, 0.05 mol) were dissolved in DMF (100 mL). To this mixture, Sodiumethoxy (NaOC$_2$H$_5$) (1.0 M solution in ethanol, 65 mL) was added dropwise. This mixture was heated to 90° C. overnight and poured into water (500 mL). The solid was collected by filtration. The solid was washed by water and recrystallized from ethanol (100 mL) to give 10.5 grams, (91.3% yield).

Example 5

General Synthesis of 4-{[N,N-dimethyl-amino]-phenylene-thien-5}-formate lithium 4-[N,N-dimethylaminophenylethenyl]thiophene (4.58 g, 0.02 mol) was dissolved into dry THF (50 mL) and cooled to −78° C. To this solution, butyllithium (8.0 mL, 0.02 mol, 2.5M in hexane) was added dropwise. The yellow solution rapidly turned green in color. The solution was slowly warmed to −20° C. (during this process, if the solution color changes back to yellow then add more BuLi) and then cooled to −78° C. Carbon dioxide (CO$_2$) gas was then bubbled through the solution for 6 hours. The THF was then evaporated in Vca. Residue was collected and washed by water. The final product was purified by recrystallization from ethanol to give 2.65 grams, (47.5% yield).

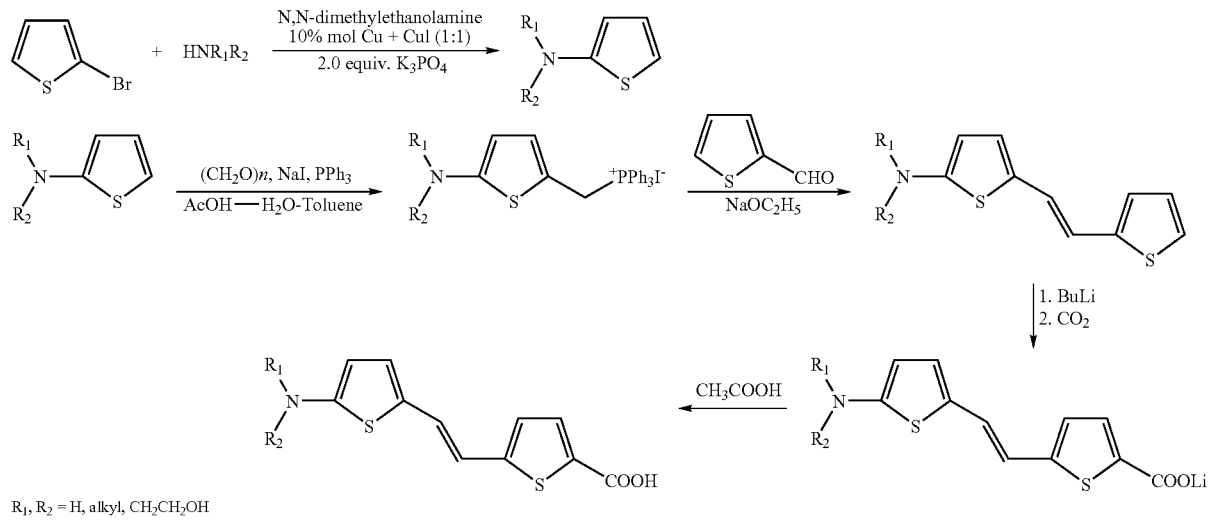

Scheme 2

R$_1$, R$_2$ = H, alkyl, CH$_2$CH$_2$OH

Example 6

General Synthesis of Phosphonium Salts

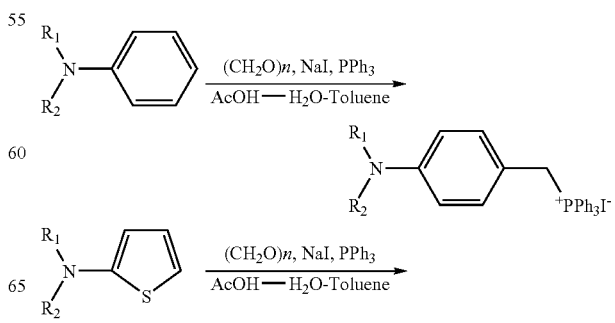

-continued

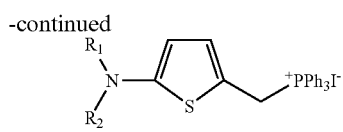

NaI (15.0 g, 0.1 mol), H₂O (7.80 ml) and HOAC (22.2 ml) were added to a solution of N,N-dialkylbenzenamine (0.1 mol), Ph₃P (26.2 g, 0.1 mol) and paraformaldehyde (3.0 g, 0.03 mol) in toluene (150 ml). The resulting mixture was refluxed for 24 h. H₂O (200 ml) was added to the mixture, extraction was performed with CH₂Cl₂, the organic layers were washed with NaHCO₃, then with H₂O, and subsequently dried over MgSO₄. The solvent was then evaporated. The residue was purified by recrystallization from Ethanol. Examples of Phosphoniums Salts are shown in Table 6.

TABLE 6

| Entry | R1 | R2 | product | Yield(%) |
|---|---|---|---|---|
| 1 | —CH₃ | —CH₃ | H₃C\N(CH₃)—C₆H₄—CH₂⁺PPh₃I⁻ | 45.89 |
| 2 | —CH₃ | —CH₂CH₂OH | HOH₂CH₂C\N(CH₃)—C₆H₄—CH₂⁺PPh₃I⁻ | 85.66 |
| 3 | —CH₂CH₂OH | —CH₂CH₂OH | HOH₂CH₂C\N(CH₂CH₂OH)—C₆H₄—CH₂⁺PPh₃I⁻ | 64.51 |
| 4 | —CH₃ | —CH₂CH₂OH | H₃C\N(CH₂CH₂OH)—thiophene—CH₂⁺PPh₃I⁻ | 43.06 |

Exemplary fluorescent dyes having Formula IV are as follows, but are not limited to:

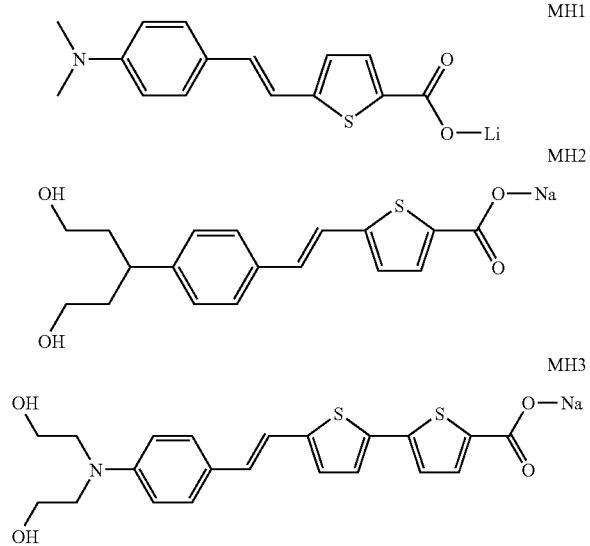

Figure 4:
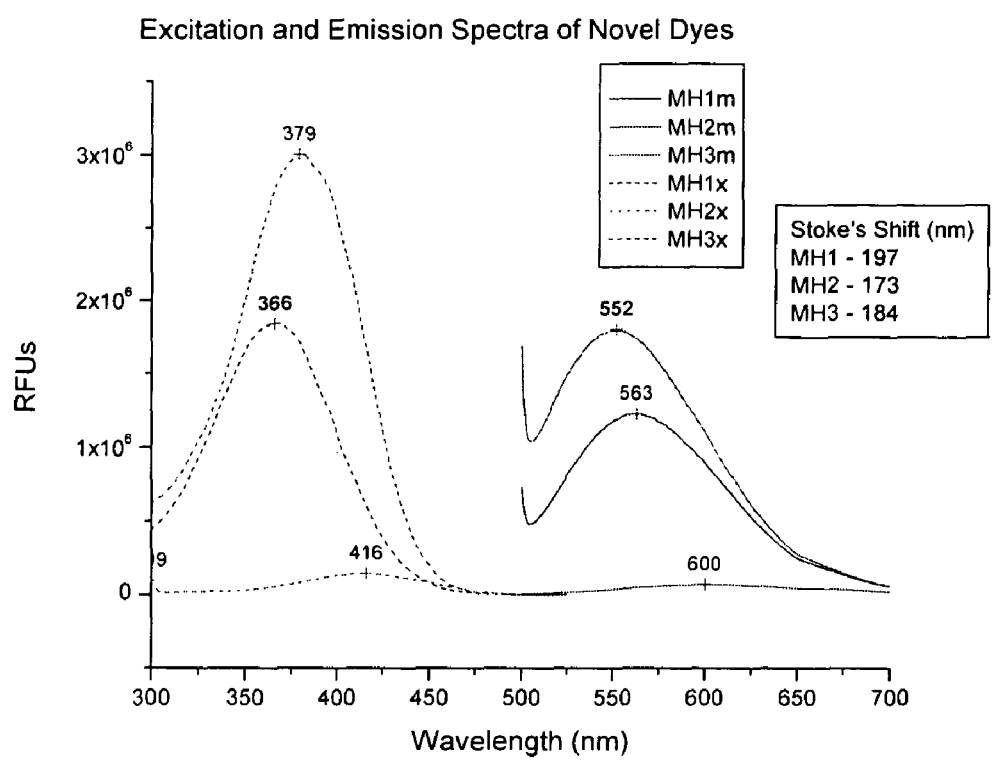
FIG. 4 is a graph showing MH1, MH2, MH3 dyes Stokes shift.

The benefit of these exemplary fluorescent dyes MH1, MH2, and MH3 is their Stokes shift as shown in FIG. 4.

Unlike Fluorescein and other commercially available dyes whose peak excitation and emission wavelengths are extremely close the MH dyes have ~200 nm between peaks.

The fluorescent dyes of the present invention show greater stability or shelf-life. That is, the fluorescence functionality of the dye is maintained when stored at room temperature in a transparent container for several months. The fluorescent dyes of the present invention can be tethered to any of the following surfaces, for example, glass, polymer, metal or any combination, provided that the electron-donating moiety or the electron-accepting moiety can react with a reactive group on the desired tethering surface. US Patent Application Publication No. 2004/0043508 A1, incorporated herein by reference in its entirety, discloses surfaces providing reactive groups suitable for tethering fluorescent dyes of the present invention. The resulting tethered surface thus becomes labeled with the fluorescent dye. The fluorescent dye is covalently bound to the surface providing an opportunity for prepackaged fluorescent dye labeled analytical devices. The analytical devices could range from a single surface wherein the fluorescent dye is covalently attached to a sophisticated device comprising an inlet for introducing a sample for analysis, which may or may not contain the target material, in fluid communication with a reaction area, wherein the fluorescent dye is covalently attached to the reaction area with a detector in proximity to the reaction area where the presence or absence of fluorescence may be evaluated. An appropriate reaction area is exemplified by the following: a microscope slide, a microarray, a flask, a capillary tube, microbeads, nanobeads, a microwell plate, a microfluidic channel, and a microfluidic reservoir. The analytical device may further comprise an outlet in fluid communication with the reaction area, for extracting material. The inlet and the outlet may occupy the same space or be the same structure, for example, a flask; or the inlet and outlet may be separate from each other or be different structures, for example, a flow through microfluidic device. The analytical device may comprise a plurality of inlets, reaction areas, detectors, and outlets. The surfaces may be coated in order to provide the reactive group needed for tethering. For example, coated microscope slides such as GAPS™ or UltraGAPS™ (trademarks of Corning Incorporated) slides could provide an appropriate surface. Appropriate surfaces could also be provided by the Epic™ (trademark of Corning Incorporated) System Microplates. The surfaces may also be membranes or they may comprise combinations of membranes with other structures, such as, but not limited to, flasks containing one or a plurality of membranes. The fluorescent dyes may also be used as filters for a target material in a biological assay by attaching the fluorescent dye to the surfaces of microbeads and nanobeads commonly used in the art. The surfaces may be of any shape or any size to provide the necessary environment for a particular application. This tethering capability may allow direct quantitation of DNA through coated surfaces such as, but not limited to, PCR plates or microplates. The fluorescent dyes of the present invention tethered to a surface would show a change in fluorescent signal with the binding of DNA generated through a process, for example, PCR generated DNA. Some of the benefits of this approach are sensitive "on-surface" readings, requiring no further addition of the fluorescent dye, and the generated PCR product can be used for subsequent applications without the need for a dye removal step.

The fluorescent dyes of the present invention appear to be more sensitive to dsDNA than to ssDNA as previously discussed. ssDNA gives the appearance of a buffer to the fluorescent dye, adding to the overall dielectric constant of the biological assay. dsDNA has hydrophilic and hydrophobic areas that change the dielectric environment and thus influence the dyes' fluorescence. Because of this sensitivity to dielectric environmental change, the fluorescent dyes of the present invention have a very small lowest detection limit (~10 ng/well in some cases) in a 96 well microplate. The fluorescence of these dyes changes through electronic reorganization based on changes in the dielectric environment to which they are introduced. These dye molecules are substantially planar in structure. The planar structure is maintained through the conjugated π-electron bridge between the electron donor and electron acceptor moieties. This differs from the commercially available fluorescent dyes, in that, many of the commercially available dyes change their fluorescence based on molecular reorientation and not electronic reorganization.

Solubility of the fluorescent dyes of the present invention may be manipulated depending on their application. The hydrophilic and hydrophobic properties of the fluorescent dyes may be changed based on the length and substituents of the electron-donating moiety and electron-accepting moiety. Typically, longer structures tend to be less hydrophilic. Solubility may also be affected by changing the functional groups other than those in the electron-donating moiety or the electron-accepting moiety associated with the various structures disclosed in the present invention. Thus, the solubility of the fluorescent dyes can be tailored to meet the specific requirements of the application.

It will be apparent to those skilled in the art that various modifications and variations can be made to the present invention without departing from the spirit or scope of the invention. Thus, it is intended that the present invention cover the modifications and variations of this invention provided they come within the scope of the appended claims and their equivalents.

The invention claimed is:

1. A fluorescent dye having Formula III:

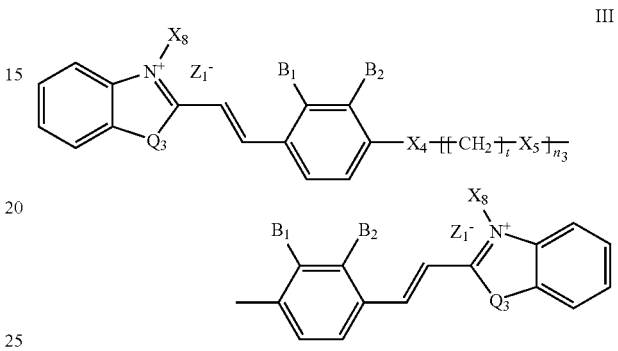

wherein:

t is an integer from 1 through 8; and $X_4$ and $X_5$ can be the same or can be different and are selected from the group consisting of O, S, N, NH, $NH_2$ and Se; and $n_3$ is an integer from 1 through 3; and $B_1$ and $B_2$ can be the same or can be different and are selected from the group consisting of H, OH, $NH_2$, Cl, and F; and $Q_3$ is O or S; and $Z_1^-$ is a monovalent anion, and further provided that when $Z_1^-$ is present, then $(CH_2)_{n6}$-$Z_2^-$ is absent; and $X_8$ is selected from the group consisting of H, $CH_3$, and $(CH_2)_{n6}$-$Z_2^-$, where $Z_2^-$ is a monovalent anion, and further provided that when $Z_2^-$ is present, then $Z_1^-$ is absent; and $n_6$ is an integer from 1 through 10.

2. A method of detecting a target material in biological assays comprising contacting the target material with the fluorescent dye of claim 1, exciting the fluorescent dye, and detecting the fluorescence.

3. A composition comprising the fluorescent dye of claim 1 and a solvent.

4. A method of synthesizing the fluorescent dye of Formula III:

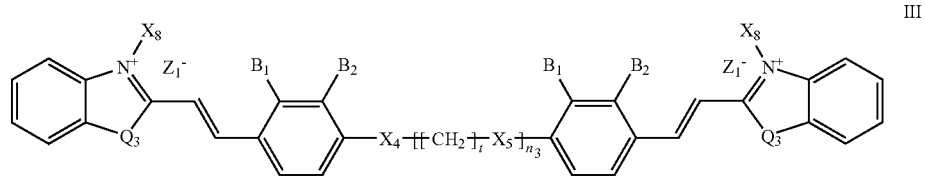

the method comprising: adding excess iodomethane to methylbenzthiazole;

isolating methylbenzthiazole salt;

dissolving the methylbenzthiazole salt in methanol to form a methylbenzthiazole solution in methanol;

adding a substituted benzaldehyde and piperidine to the methylbenzthiazole solution in methanol; and isolating the reaction product and recrystallizing a solid from the solution; wherein in Formula III;

t is an integer from 1 through 8; and $X_4$ and $X_5$ can be the same or can be different and are selected from the group consisting of O, S, N, NH, $NH_2$ and Se; and $n_3$ is an integer from 1 through 3; and $B_1$ and $B_2$ can be the same or can be different and are selected from the group consisting of H, OH, $NH_2$, Cl, and F; and $Q_3$ is O or S; and $Z_1^-$ is a monovalent anion, and further provided that when $Z_1^-$ is present, then $(CH_2)_{n6}$-$Z_2^-$ is absent; and $X_8$ is selected from the group consisting of H, $CH_3$, and $(CH_2)_{n6}$-$Z_2^-$, where $Z_2^-$ is a monovalent anion, and further provided that when $Z_2^-$ is present, then $Z_1^-$ is absent; and $n_6$ is an integer from 1 through 10.

5. An analytical device comprising: at least one reaction area which is covalently labeled with the fluorescent dye of claim 1 that fluoresces when in contact with a specific target material, said at least one reaction area being disposed for contact with a sample and at least one detector in proximity to said at least one reaction area for detecting the presence or absence of fluorescence.

6. The analytical device of claim 5, wherein said at least one reaction area comprises a glass surface covalently labeled with the fluorescent dye.

7. The analytical device of claim 5, wherein said at least one reaction area comprises a polymer surface covalently labeled with the fluorescent dye.

8. The analytical device of claim 5, wherein said at least one reaction area comprises a metal surface covalently labeled with the fluorescent dye.

9. The analytical device of claim 5, further comprising a plurality of reaction areas in series with respect to each other.

10. The analytical device of claim 5, further comprising a plurality of reaction areas in parallel with respect to each other.

11. The analytical device of claim 5, wherein said at least one reaction area is selected from the group consisting of a microscope slide, a microarray, a flask, a capillary tube, microbeads, nanobeads, a microwell plate, a microfluidic channel, and a microfluidic reservoir.

12. The fluorescent dye of claim 1, wherein:

$Z_1^-$ is selected from the group consisting of OH, SH, $HCO_3$, $HSO_3$, $HSO_4$, $H_2PO_4$, $PF_6$, F, CNO, SCN, tetraphenyl borate, $BH_4$, Cl, I, Br, $BF_4$, $I_3$, $NO_3$, $SO_3$, BrO, $BrO_2$, $BrO_3$, $BrO_4$, IO, $IO_2$, $IO_3$, $IO_4$, ClO, $ClO_2$, $ClO_3$, and $ClO_4$.

13. The fluorescent dye of claim 1, wherein:

$Z_2^-$ is selected from the group consisting of O, S, $CO_2$, $PO_3$, $PF_6$, F, $SO_3$, and $NO_2$.

14. The fluorescent dye of claim 1, having the following formula:

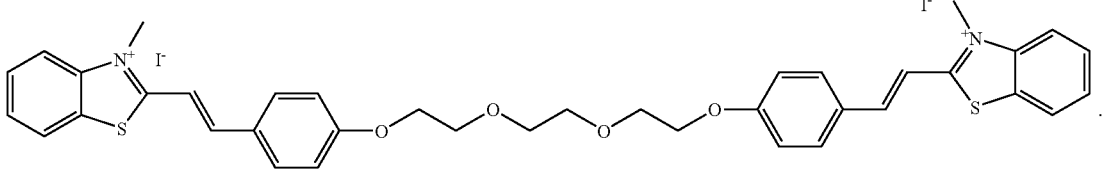

* * * * *